(12) United States Patent
Xie et al.

(10) Patent No.: US 12,364,438 B1
(45) Date of Patent: Jul. 22, 2025

(54) METHOD FOR DETERMINING VALIDITY OF EMG SIGNAL, APPARATUS, DEVICE AND STORAGE MEDIUM

(71) Applicant: Guangdong University of Technology, Guangdong (CN)

(72) Inventors: Shengli Xie, Guangdong (CN); Zuyuan Yang, Guangdong (CN); Jia Chen, Guangdong (CN); Junjie Yang, Guangdong (CN); Kan Xie, Guangdong (CN); Wenfang Bai, Guangdong (CN); Victor Fedorovich Kuzin, Moscow (RU)

(73) Assignee: Guangdong University of Technology, Guangzhou (CN)

( * ) Notice: Subject to any disclaimer, the term of this patent is extended or adjusted under 35 U.S.C. 154(b) by 0 days.

(21) Appl. No.: 18/988,795

(22) Filed: Dec. 19, 2024

(30) Foreign Application Priority Data

Mar. 27, 2024  (CN) .................. 202410354869.X

(51) Int. Cl.
| | | |
|---|---|---|
| A61B 5/00 | (2006.01) | |
| A61B 5/107 | (2006.01) | |
| A61B 5/395 | (2021.01) | |
| G06T 7/00 | (2017.01) | |
| G06T 7/60 | (2017.01) | |

(52) U.S. Cl.
CPC .......... *A61B 5/7221* (2013.01); *A61B 5/1071* (2013.01); *A61B 5/395* (2021.01); *A61B 5/7264* (2013.01); *G06T 7/0012* (2013.01); *G06T 7/60* (2013.01); *G06T 2207/10016* (2013.01); *G06T 2207/30004* (2013.01)

(58) Field of Classification Search
CPC ..... A61B 5/7221; A61B 5/1071; A61B 5/395; A61B 5/7264; G06T 7/0012; G06T 7/60; G06T 2207/10016; G06T 2207/30004
See application file for complete search history.

(56) References Cited

U.S. PATENT DOCUMENTS

2019/0362139 A1   11/2019   Mehl et al.

FOREIGN PATENT DOCUMENTS

| CN | 114795831 A | 7/2022 |
| CN | 117333932 A | 1/2024 |
| CN | 117532609 A | 2/2024 |

*Primary Examiner* — Jeffrey G. Hoekstra

(57) ABSTRACT

The present application provides a method for determining the validity of an electromyographic (EMG) signal, an apparatus, a device and a storage medium. The method includes: collecting video data including squatting and foot-padding by dynamic muscle stimulation of a leg, and collecting an EMG signal on a surface of the leg while squatting and foot-padding; performing human body recognition on each frame of images of the video data, and acquiring normalized coordinates of human body key points in each frame of images; converting the normalized coordinates of the human body key points in each frame of images into pixel coordinates to obtain the pixel coordinates of the human body key points in each frame of images; and correcting the pixel coordinates of the human body key points in each frame of images according to shooting angles.

18 Claims, 5 Drawing Sheets

METHOD FOR DETERMINING VALIDITY OF EMG SIGNAL, APPARATUS, DEVICE AND STORAGE MEDIUM

CROSS-REFERENCE TO RELATED APPLICATION

This application claims priority of Chinese Patent Application No. 202410354869.X, filed on Mar. 27, 2024, the entire contents of which are incorporated herein by reference.

TECHNICAL FIELD

The present application relates to the technical field of data processing, and particularly relates to a method for determining the validity of an electromyographic (EMG) signal, an apparatus, a device and a storage medium.

BACKGROUND

Existing methods for collecting EMG signals on a surface of a leg generally use the human body leg to perform some actions, such as using repeated knee extension in sitting position to dynamically excite muscles of the leg and collecting the EMG signals on the surface induced by leg movements by an EMG signal acquisition device on the leg surface. In the prior art, when performing leg muscle stimulation, a subject is required to keep the same motion amplitude and motion speed as much as possible during the leg motion. This requirement has great subjective difference for different subjects, resulting in no accurate motion standard, which may affect the accuracy of output, thus resulting in collecting an invalid EMG signal, affecting the quality of EMG signal, and further affecting the accuracy of subsequent EMG signal processing (such as motion prediction and motion control based on EMG information).

SUMMARY

The present application provides a method for determining the validity of an EMG signal, an apparatus, a device and a storage medium, which is used for determining whether the collected EMG signal is valid, improving the quality of the EMG signal, thereby improving the accuracy of the subsequent processing process of the EMG signal.

In view of this, a first aspect of the present application provides a method for determining the validity of an EMG signal, including:
  collecting video data including squatting and foot-padding by dynamic muscle stimulation of a leg, and collecting an EMG signal on a surface of the leg while squatting and foot-padding;
  performing human body recognition on each frame of images of the video data, and acquiring normalized coordinates of human body key points in each frame of images;
  converting the normalized coordinates of the human body key points in each frame of images into pixel coordinates to obtain the pixel coordinates of the human body key points in each frame of images;
  correcting the pixel coordinates of the human body key points in each frame of images according to shooting angles to obtain the corrected pixel coordinates of the key points in each frame of images;
  calculating a leg angle in each frame of images according to the corrected pixel coordinates of the key points in each frame of images to obtain angle data, the leg angles including a thigh bending angle and a foot-padding angle; and
  determining whether the EMG signal is valid through the angle data.

Alternatively, the converting the normalized coordinates of the human body key points in each frame of images into pixel coordinates to obtain the pixel coordinates of the human body key points in each frame of images includes:
  converting, according to a length and a width of each frame of images, the normalized coordinates of the human body key points in each frame of images into the pixel coordinates to obtain the pixel coordinates of the human body key points in each frame of images.

Alternatively, the correcting the pixel coordinates of the human body key points in each frame of images according to shooting angles to obtain the corrected pixel coordinates of the key points in each frame of images includes:
  calculating a ratio of a vertical coordinate value of the pixel coordinate of the human body key point in each frame of images to a cosine value corresponding to the shooting angle to obtain the corrected pixel coordinates of the key points in each frame of images.

Alternatively, the calculating the thigh bending angle in each frame of images according to the corrected pixel coordinates of the key points in each frame of images, include:
  acquiring pixel coordinates of hip joint key points, pixel coordinates of ankle key points and pixel coordinates of knee key points in each frame of images from the corrected pixel coordinates of the key points in each frame of images;
  calculating three segments of distances among three key points of the hip joint, ankle and knee in each frame of images according to the pixel coordinates of the hip joint key points, the pixel coordinates of the ankle key points and the pixel coordinates of the knee key points in each frame of images; and
  calculating the thigh bending angle in each frame of images according to the three segments of distances among the three key points of the hip joint, ankle and knee in each frame of images.

Alternatively, the calculating the foot-padding angle in each frame of images according to the corrected pixel coordinates of the key points in each frame of images, includes:
  acquiring pixel coordinates of heel key points in each frame of images from the corrected pixel coordinates of the key points in each frame of images; and
  calculating a foot-padding angle in each frame of images according to the pixel coordinates of the heel key points in each frame of images.

Alternatively, the calculating a leg angle in each frame of images according to the corrected pixel coordinates of the key points in each frame of images to obtain angle data further includes: optimizing the angle data, specifically including:
  dividing the angle data in each period into a rising signal and a falling signal, and constructing a state prediction equation of the rising signal and a state prediction equation of the falling signal in each period;
  constructing a covariance matrix, an observation noise matrix and a measurement matrix;
  calculating a filtering gain by the covariance matrix, the observation noise matrix and the measurement matrix;
  optimizing the state prediction equation in a current period by the filtering gain; and updating the covariance matrix and returning the step of calculating the filtering gain by the covariance matrix, the observation noise matrix and the measurement matrix until the angle data in all periods is optimized.

Alternatively, the updating the covariance matrix includes:

determining whether a current moment is at a boundary point of the current period, if not, a current covariance matrix being updated according to a current filtering gain and the measurement matrix; and if so, a current covariance matrix being updated as an initial value of the covariance matrix.

A second aspect of the present application provides an apparatus for determining the validity of an EMG signal, including:

a data collection unit, configured to collect video data including squatting and foot-padding by dynamic muscle stimulation of a leg, and collect an EMG signal on a surface of the leg while squatting and foot-padding;

an identification unit, configured to perform human body recognition on each frame of images of the video data, and acquire normalized coordinates of human body key points in each frame of images;

a coordinate conversion unit, configured to convert the normalized coordinates of the human body key points in each frame of images into pixel coordinates to obtain the pixel coordinates of the human body key points in each frame of images;

a coordinate correction unit, configured to correct the pixel coordinates of the human body key points in each frame of images according to shooting angles to obtain the corrected pixel coordinates of the key points in each frame of images;

a calculation unit, configured to calculate a leg angle in each frame of images according to the corrected pixel coordinates of the key points in each frame of images to obtain angle data, the leg angles including a thigh bending angle and a foot-padding angle; and a determination unit, configured to determine whether the EMG signal is valid through the angle data.

A third aspect of the present application provides an electronic device, including a processor and a memory, the memory being configured to store a program code and transmit the program code to the processor; and the processor being configured to execute the method for determining the validity of an EMG signal according to any one of the first aspect according to instructions in the program code.

A fourth aspect of the present application provides a computer-readable storage medium for storing a program code which, when executed by a processor, implements the method for determining the validity of an EMG signal according to any one of the first aspect.

As can be seen from the above technical solutions, the present application has the following advantages.

In the present application, a method for determining the validity of an EMG signal is provided, including: collecting video data including squatting and foot-padding by dynamic muscle stimulation of a leg, and collecting an EMG signal on a surface of the leg while squatting and foot-padding; performing human body recognition on each frame of images of the video data, and acquiring normalized coordinates of human body key points in each frame of images; converting the normalized coordinates of the human body key points in each frame of images into pixel coordinates to obtain the pixel coordinates of the human body key points in each frame of images; correcting the pixel coordinates of the human body key points in each frame of images according to shooting angles to obtain the corrected pixel coordinates of the key points in each frame of images; and calculating a leg angle in each frame of images according to the corrected pixel coordinates of the key points in each frame of images to obtain angle data, the leg angles including a thigh bending angle and a foot-padding angle, it being determined whether the EMG signal is valid through the angle data.

In the present application, the video data of leg motions are collected at the same time as the EMG signal, and the angle data of the leg is acquired through the video data, and the validity of the collected EMG signal is determined through the angle data, to determine the collection quality of the EMG signal and improve the accuracy of the subsequent EMG signal processing. In the present application, it is further considered that the coordinates of the key points obtained by human body recognition are normalized coordinates, and a coordinate system of each of frames is transformed. If the leg angle is calculated directly based on the normalized coordinates, there is a problem of complicated calculation process. In order to improve this problem, the normalized coordinates are converted into the pixel coordinates, and a shooting error is corrected by an shooting angle. At this time, a pixel coordinate system of each of frames is fixed, which simplifies the calculation process of leg angles and improves the calculation efficiency.

BRIEF DESCRIPTION OF THE DRAWINGS

To explain examples of the present application or technical solutions in the prior art more clearly, a brief description will be given below with reference to accompanying drawings which are used in the description of the examples or the prior art. Obviously, the drawings in the description below are merely some examples of the present application, and for those of ordinary skill in the art, other accompanying drawings can be obtained according to the accompanying drawings without creative efforts.

DETAILED DESCRIPTION

In order to make those skilled in the art better understand the solutions of the application, technical solutions in examples of the present application will be described clearly and completely in the following with reference to the attached drawings in the examples of the present application. Obviously, all the described examples are only some, rather than all examples of the present application. Based on the examples in the present application, all other examples obtained by those of ordinary skill in the art without creative efforts belong to the scope of protection of the present application.

Figure 1:
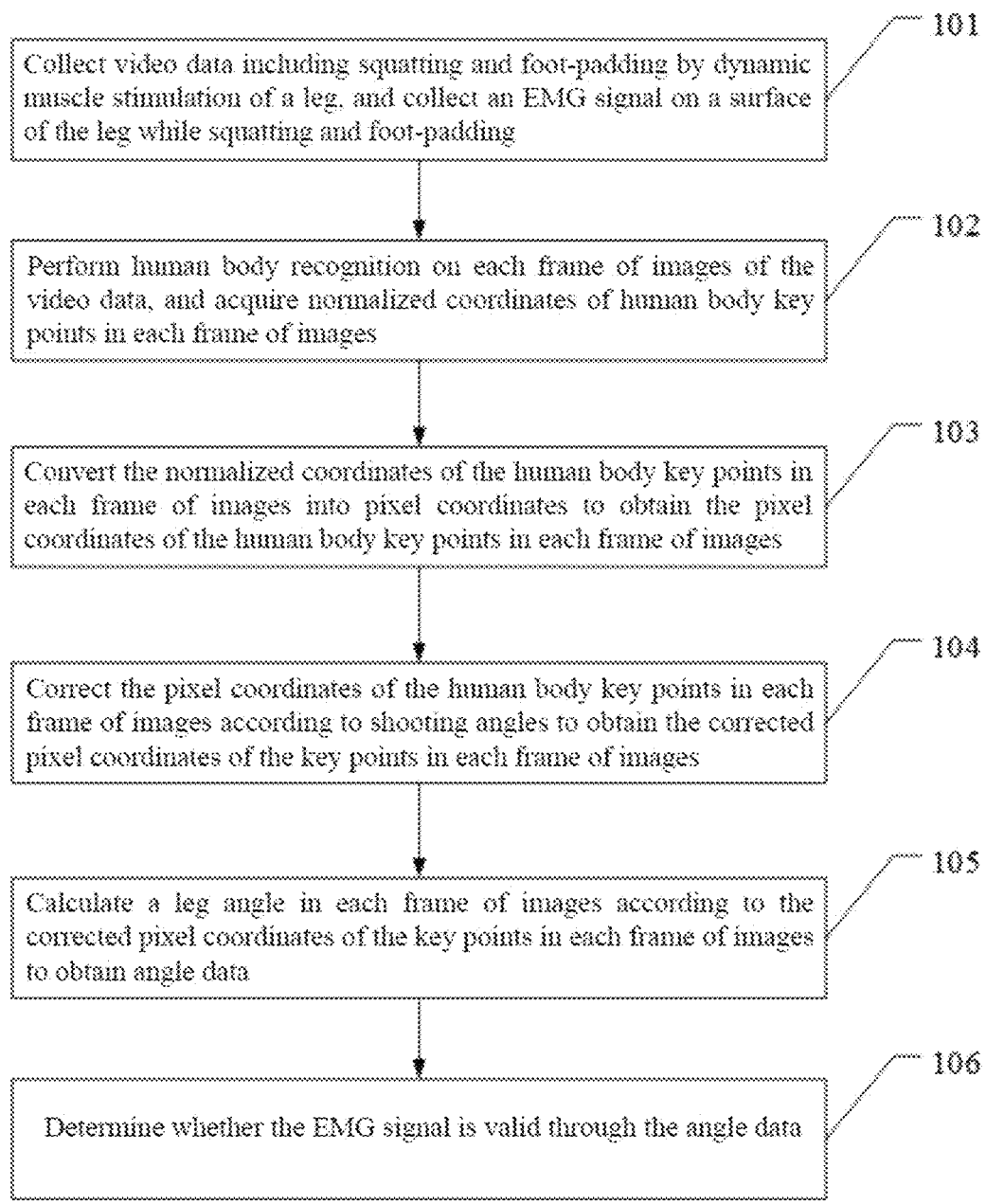
FIG. 1 is a schematic flow chart of a method for determining the validity of an EMG signal provided by an example of the present application.

In order to facilitate understanding, referring to FIG. 1, an example of the present application provides a method for determining the validity of an EMG signal, including the following steps.

In step 101, video data including squatting and foot-padding by dynamic muscle stimulation of a leg is collected, and an EMG signal on a surface of the leg is collected while squatting and foot-padding.

A subject can complete squatting and foot-padding with dynamic leg muscle excitation and record the video data of the squatting and foot-padding with dynamic leg muscle excitation, collect the EMG signal on the surface of the leg while squatting and foot-padding, and collect the EMG signal through the existing EMG signal collection device. The squatting and foot-padding by dynamic muscle stimulation of the leg is to perform multiple groups of repeated movements to achieve the purpose of stimulating the main contraction muscles of the leg. In this effective stimulation process, a suitable EMG signal can be collected, if there are pain muscles, and it can be ensured a suitable pain signal is collected in the EMG signal through comparison. At this time, the collected EMG information including a pain signal can be used to observe the effect of pain stimulation on muscle activity, human body leg pain detection, etc.

In step 102, human body recognition is performed on each frame of images of the video data, and normalized coordinates of human body key points in each frame of images are acquired.

Human body recognition is performed on each frame of images of the video data, and normalized coordinates of human body key points of each frame of images are acquired; and the specific recognition process of the key points can refer to the prior art, and the specific process thereof will not be described in detail here.

In step 103, the normalized coordinates of the human body key points are converted in each frame of images into pixel coordinates to obtain the pixel coordinates of the human body key points in each frame of images.

Since the coordinates of the human body key points acquired after human body recognition are normalized coordinates, a normalized coordinate axis where these key points are located changes with the movement of the subject, which leads to the failure to associate the previous and subsequent frames in the video data, and it is also impossible to determine the specific meaning represented by a coordinate value of a normalized coordinate of each human key point. This problem is solved by the pixel coordinate, which is a coordinate of each pixel point in the image. The advantage of the pixel coordinate is that it can fix the coordinate axis of the image of each frame, an original point of the pixel coordinate is an upper left corner point of the image, an x-axis is established horizontally to the right, and a y-axis is established vertically to the lower, so that the image of each frame is associated, and each frame can calculate an angle value with the same calculation method for the key point of the leg. Therefore, in an example of the present application, the normalized coordinates are converted into pixel coordinates to simplify the subsequent calculation process and improve the calculation efficiency.

According to a length and a width of each frame of images, the normalized coordinates of the human body key points in each frame of images can be converted into the pixel coordinates to obtain the pixel coordinates of the human body key points in each frame of images. Specifically, the acquired normalized coordinates of the human body key points can be multiplied by the length and width of the image, so that the normalized coordinates within a range of [0,1] can be converted into actual pixel coordinates.

In step 104, the pixel coordinates of the human body key points in each frame of images are corrected according to shooting angles to obtain the corrected pixel coordinates of the key points in each frame of images.

Figure 2:
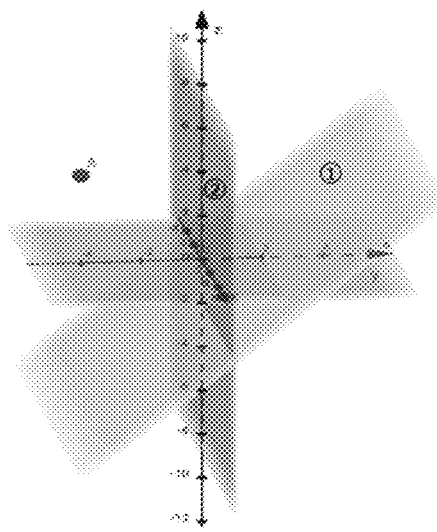
FIG. 2 is a schematic diagram of an actual shooting process from a third view provided by an example of the present application.
Figure 3:
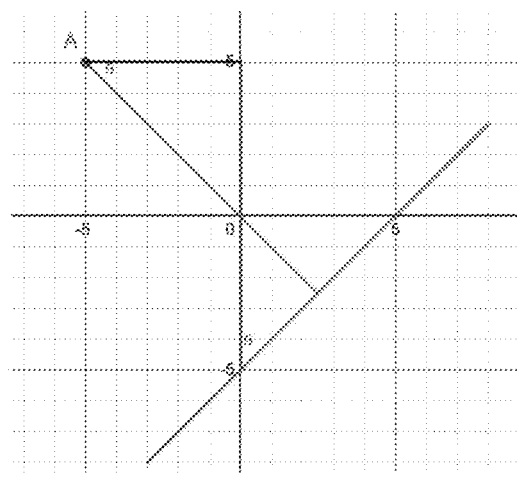
FIG. 3 is another schematic diagram of an actual shooting process from a third view provided by an example of the present application.

There is a shooting error caused by a shooting angle $\theta$ when the normalized coordinates are converted into the pixel coordinates by the above method, that is, there is an inclination angle between photographed characters and those in the real world, as shown in FIG. 2, a point A is a shooting point, the picture obtained by shooting is a picture on a plane (1) in FIG. 2, while a picture in the real world is a picture on a plane (2) in FIG. 2 (namely, a plane where a z axis is located), and it can be seen from FIG. 3 that this inclination angle is an included angle $\theta$ between two planes. In order to avoid the shooting error, the shooting angle $\theta$ can be fixed firstly, and a coordinate value (x, y) of the pixel coordinate of the human body key point can be obtained by using coordinate conversion. It can be seen from an angle relationship in FIG. 3 that the fixed shooting angle $\theta$ only affects a vertical coordinate value of the pixel coordinate of the human body key point; and a ratio of a vertical coordinate value of the pixel coordinate of the human body key point in each frame of images to a cosine value corresponding to the shooting angle can be calculated to obtain the corrected pixel coordinate of the key point in each frame of images. A y coordinate error can be corrected by dividing a y coordinate value of the obtained pixel coordinate of the human body key point by a cosine value of the shooting angle $\theta$, i.e., $y'=y/\cos\theta$, to obtain the corrected pixel coordinate (x, y') of the key point.

In step 105, a leg angle in each frame of images is calculated according to the corrected pixel coordinates of the key points in each frame of images to obtain angle data.

Leg angles include a thigh bending angle and a foot-padding angle. The thigh bending angle needs to calculate the three-segment distance among the three key points of a human body hip joint, a knee and an ankle, and the foot-padding angle needs to acquire the pixel coordinate of the heel key point.

In an example of the present application, the thigh bending angle in each frame of images being calculated according to the corrected pixel coordinates of the key points in each frame of images includes the following steps.

In A1, pixel coordinates of hip joint key points, pixel coordinates of ankle key points and pixel coordinates of knee key points in each frame of images are acquired from the corrected pixel coordinates of the key points in each frame of images.

In A2, three segments of distances among three key points of the hip joint, ankle and knee in each frame of images are calculated according to the pixel coordinates of the hip joint key points, the pixel coordinates of the ankle key points and the pixel coordinates of the knee key points in each frame of images.

Taking a right leg as an example, when calculating three segments of distances among three key points of the hip joint, the ankle and the knee in each frame of images, an original point is at a knee, assuming that a distance from the knee to the hip joint is $d_1$, a distance from the knee to the ankle is $d_2$, a distance from the hip joint to the ankle is $d_3$, a pixel coordinate of the hip joint key point is $(x_1, y_1')$, and the pixel coordinate of the ankle key point is $(x_2, y_2')$; and the distance da from the hip to the ankle is calculated as:

$$d_3 = \sqrt{(x_1{}^2 - x_2{}^2) + (y''_1{}^2 - y'_2{}^2)}.$$

By the same reasoning, the distance $d_1$ from the knee to the hip joint and the distance $d_2$ from the knee to the ankle can be obtained, and the specific calculation process is similar to the calculation process of the distance da from the hip joint to the ankle, which will not be described in detail herein.

In A3, the thigh bending angle in each frame of images is calculated according to the three segments of distances among the three key points of the hip joint, ankle and knee in each frame of images.

Taking a right leg as an example, the thigh bending angle in each frame of images is calculated according to the three segments of distances among the three key points of the hip joint, ankle and knee in each frame of images:

$$\alpha = \arccos \frac{d_1^2 + d_2^2 - d_3^2}{2 d_1 d_2}$$

where $\alpha$ is a thigh bending angle.

In an example of the present application, the foot-padding angle in each frame of images being calculated according to the corrected pixel coordinates of the key points in each frame of images, includes the following steps:

In B1, pixel coordinates of heel key points in each frame of images are acquired from the corrected pixel coordinates of the key points in each frame of images; and In B2, a foot-padding angle in each frame of images is calculated according to the pixel coordinates of the heel key points in each frame of images.

Taking a right foot as an example, when calculating the foot-padding angle, an origin point is at a right toe, and assuming that a pixel coordinate of a heel key point is (x, y'), the calculation process of the foot-padding angle is:

$$\beta = \arctan \frac{y'}{x}$$

where $\beta$ is a foot-padding angle.

Thanks to the advantage of the pixel coordinates, the calculation of the leg angle for each frame can be done in the above-mentioned manner.

Figure 4:
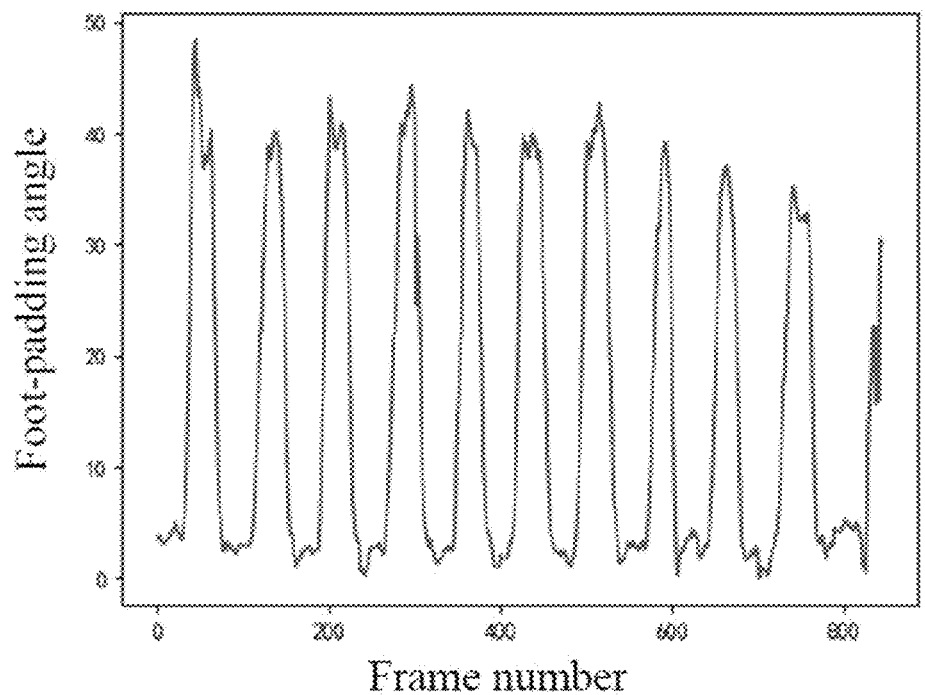
FIG. 4 is a curve graph of foot-padding angles provided by an example of the present application.
Figure 5:
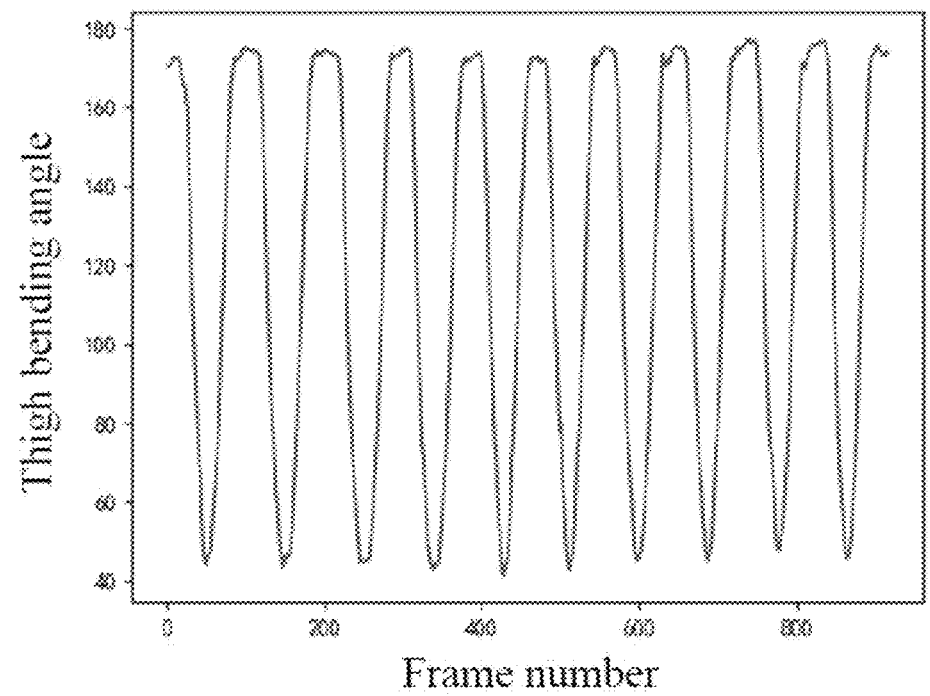
FIG. 5 is a curve graph of thigh bending angles provided by an example of the present application.

The calculation process is not complicated, and the calculation efficiency is high. The two-dimensional angle curve change graph of frame number-foot-padding angle and frame number-thigh bending angle can be counted, as shown in FIGS. 4 and 5.

In step 106, it is determined whether the EMG signal is valid through the angle data.

Whether the collected EMG signal is valid can be determined according to the angle change curve graphs of the thigh bending angle and the foot-padding angle. After a normal person completes several sets of squatting and foot-padding, an output angle change curve graph exhibits periodicity. If the output image is irregular or non-periodic, it may be caused by irregular movements. At this time, the collected EMG signal is invalid, and the subject needs to complete the movements all over again and collect data again.

In an example of the present application, the video data of leg movements are collected at the same time as the EMG signal, and the angle data of the leg is acquired through the video data, and the validity of the collected EMG signal is determined through the angle data, to determine the collection quality of the EMG signal and improve the accuracy of the subsequent EMG signal processing. In the present application, it is further considered that the coordinates of key points obtained by human body recognition are normalized coordinates, and a coordinate system of each of frames is transformed. If the leg angle is calculated directly based on the normalized coordinates, there is a problem of complicated calculation process. In order to improve this problem, the normalized coordinates are converted into the pixel coordinates, and the shooting error is corrected by the shooting angle. At this time, a pixel coordinate system of each of frames is fixed, which simplifies the calculation process of leg angles and improves the calculation efficiency.

The above is one example of a method for determining the validity of an EMG signal provided in the present application, and the following is another example of a method for determining the validity of an EMG signal provided in the present application.

Figure 6:
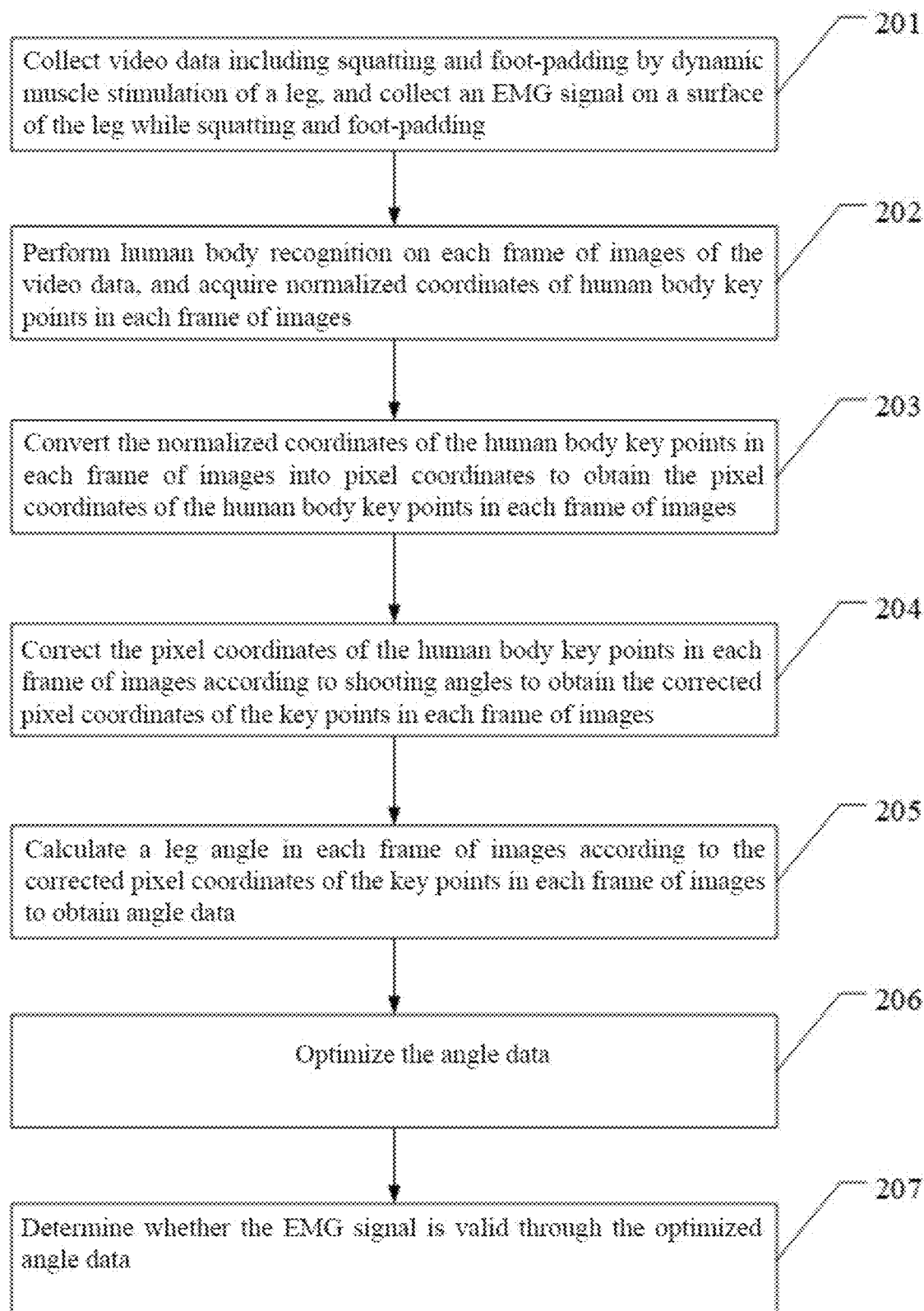
FIG. 6 is another schematic flow chart of the method for determining the validity of an EMG signal provided by an example of the present application.

Referring to FIG. 6, a method for determining the validity of an EMG signal provided by an example of the present application includes:

In step 201, video data including squatting and foot-padding is collected by dynamic muscle stimulation of a leg, and an EMG signal on a surface of the leg is collected while squatting and foot-padding.

In step 202, human body recognition is performed on each frame of images of the video data, and normalized coordinates of human body key points in each frame of images are acquired.

In step 203, the normalized coordinates of the human body key points in each frame of images are converted into pixel coordinates to obtain the pixel coordinates of the human body key points in each frame of images.

In step 204, the pixel coordinates of the human body key points in each frame of images are corrected according to shooting angles to obtain the corrected pixel coordinates of the key points in each frame of images.

In step 205, a leg angle in each frame of images is calculated according to the corrected pixel coordinates of the key points in each frame of images to obtain angle data.

The specific contents of steps 201 to 205 in the example of the present application are consistent with the specific contents of the preceding steps 101 to 105, and the detailed description thereof will not be repeated here.

In step 206, the angle data is optimized.

Before the analysis of EMG signal, the preliminary collected angle data needs to be optimized. The change of angle exhibits periodic changes and there is some noise interference. A signal filter based on a periodic signal is used to improve the accuracy and stability of the change of angle.

The signal filter based on the periodic signal optimizes the angle data, and the nonlinear periodic signal is converted into two linear signals. For example, the signal in one cycle of the foot-padding motion varies from non-angular to angular to non-angular, so that the signal in one cycle can be split into a segment of rising signal and a segment of falling signal, which converts the non-linear signal analysis into a linear signal analysis. Therefore, before the signal is input, two initial values need to be determined, one for a new signal at a boundary point of rising and falling signals and another one for a covariance matrix P. The time of a period can be determined by taking a mean value according to the number of video frames and the number of periodic changes, because the action is carried out at a uniform speed, the time of the boundary point is half a cycle, and the angle value corresponding to this point is an initial value of the new signal.

At each boundary point, the covariance matrix is updated back to the initial value and continuously updated according to the filtering gain.

In an example of the present application, the specific process of optimizing the angle data may be:

In S2061, the angle data in each period is divided into a rising signal and a falling signal, and a state prediction equation of the rising signal and a state prediction equation of the falling signal in each period are constructed.

A state prediction equation for a rising signal is:

$$x_t = \begin{bmatrix} \theta_t \\ w_t \end{bmatrix} = \begin{bmatrix} 1 & \Delta t \\ 0 & 1 \end{bmatrix} \begin{bmatrix} \theta_{t-1} \\ w_{t-1} \end{bmatrix} = A_1 * x_{t-1}; \text{ and}$$

A state prediction equation for a falling signal is:

$$x_t = \begin{bmatrix} \theta_t \\ w_t \end{bmatrix} = \begin{bmatrix} 1 & -\Delta t \\ 0 & -1 \end{bmatrix} \begin{bmatrix} \theta_{t-1} \\ w_{t-1} \end{bmatrix} = A_2 * x_{t-1}$$

where $\Delta t$ is a time of each frame of images, $\theta_t$ is an angle value at a moment t, $w_t$ is an angular velocity at a moment t, and $$A_1 = \begin{bmatrix} 1 & \Delta t \\ 0 & 1 \end{bmatrix} \text{ and } A_2 = \begin{bmatrix} 1 & -\Delta t \\ 0 & -1 \end{bmatrix}$$

are state transition matrices.

In S2062, a covariance matrix P, an observation noise matrix R and a measurement matrix H are constructed.

An initial value P0 of the covariance matrix is pre-set, and is set according to the actual situation, and the constructed covariance matrix satisfies:

$$P_t = A P_{t-1} A^T + Q$$

where $P_t$ is a covariance matrix at a moment t, $P_{t-1}$ is a covariance matrix at a moment t−1, A is a state transition matrix, and Q is a noise matrix.

In S2063, a filtering gain K is calculated by the covariance matrix P, the observation noise matrix R and the measurement matrix H.

The filtering gain is calculated as:

$$K_t = P_t H^T (H P_t H^T + R)^{-1}$$

where $K_t$ is a filtering gain at a moment t.

In S2064, the state prediction equation in a current period is optimized by the filtering gain.

The state prediction equation in a current period is optimized by the filtering gain, and a best estimated value $X_t$ at each moment is outputted, namely:

$$X_t = X_t + K_t (Z_t - H X_t)$$

where $X_t$ is a best estimated value and $Z_t$ is an actual measured value.

In S2065, the covariance matrix is updated and the step of calculating the filtering gain is returned by the covariance matrix, the observation noise matrix and the measurement matrix until the angle data in all periods is optimized.

It is determined whether a current moment is at a boundary point of the current period, if not, a current covariance matrix being updated according to a current filtering gain and the measurement matrix; and if so, a current covariance matrix being updated as an initial value of the covariance matrix.

If a current moment is a boundary point of a current period, a current covariance matrix is updated to an initial value, namely:

$$P_t = P_0.$$

If a current moment is not at a boundary point of a current period, the current covariance matrix is updated according to a current filtering gain and the measurement matrix, namely:

$$P_t = (I - K_t H) P_t.$$

After repeating the above steps, the angle change curve can be optimized, to obtain a smoother angle change curve graph. Multiple sets of periodic movements are now presented on the smooth periodic angle change graph. Thanks to the effective muscle stimulation, some interference of movement deformation or movement caused by muscle fatigue can preliminarily be excluded by means of large amplitude mutation of angles, to ensure that a sufficiently accurate EMG signal is collected. Most importantly, by comparing the angle change curve graph, it is possible to find that there are some small-scale mutation angles in the graph, which may be bending obstacle or foot-padding obstacle caused by pain, thus ensuring that some pain signals are contained in the collected EMG signal. Moreover, an approximate range of pain signal generation can be determined, ensuring that pain signal is present in the post-processed EMG signal.

In an example of the present application, the angle data is acquired and optimized by adding pixel coordinates and periodic filtering, which can not only eliminate the interference of human body physiological factors existing in the traditional EMG acquisition through the large mutation of the angle, resulting in inaccurate pain signal acquisition or no pain signal, but also ensure that the collected EMG signal contains a pain signal according to the small mutation of the angle caused by pain in the optimized angle change graph.

In step 207, it is determined whether the EMG signal is valid through the optimized angle data.

It can be determined whether there is a pain signal in the EMG signal through the optimized angle data. If it is required that the EMG signal contains a pain signal in the subsequent processing, and there is no pain signal in the actually collected EMG signal, it is determined that the acquired EMG signal is invalid, and the EMG signal needs to be re-collected; on the contrary, if there is a pain signal in the EMG signal and the angle change curve graph shows periodicity, it is determined that the acquired EMG signal is valid.

In an example of the present application, the video data of leg movements are collected at the same time as the EMG signals, and the angle data of the leg is acquired through the video data, and the validity of the collected EMG signal is determined through the angle data, to determine the collection quality of the EMG signal and improve the accuracy of the subsequent EMG signal processing. In the present application, it is further considered that the coordinates of key points obtained by human body recognition are normalized coordinates, and a coordinate system of each of frames is transformed. If the leg angle is calculated directly based on the normalized coordinates, there is a problem of complicated calculation process. In order to improve this problem, the normalized coordinates are converted into pixel coordinates, and the shooting error is corrected by the shooting angle. At this time, a pixel coordinate system of each of frames is fixed, which simplifies the calculation process of leg angles and improves the calculation efficiency.

Further, in an example of the present application, a smoother angle change curve graph can be obtained by performing optimization processing on the angle data, and some interference of motion deformation or movement caused by muscle fatigue can be preliminarily excluded by means of a large amplitude mutation of the angle in the angle change curve graph to ensure that a sufficiently accurate EMG signal is collected. It is also feasible to determine whether there are some angles of small-scale mutation in the graph by comparing the angle change curve graph, and these angles may be bending obstacle or foot-padding obstacle caused by pain, to determine whether there is partial pain signal in the collected EMG signal, which contributes to the accuracy of subsequent EMG signal processing.

Figure 7:
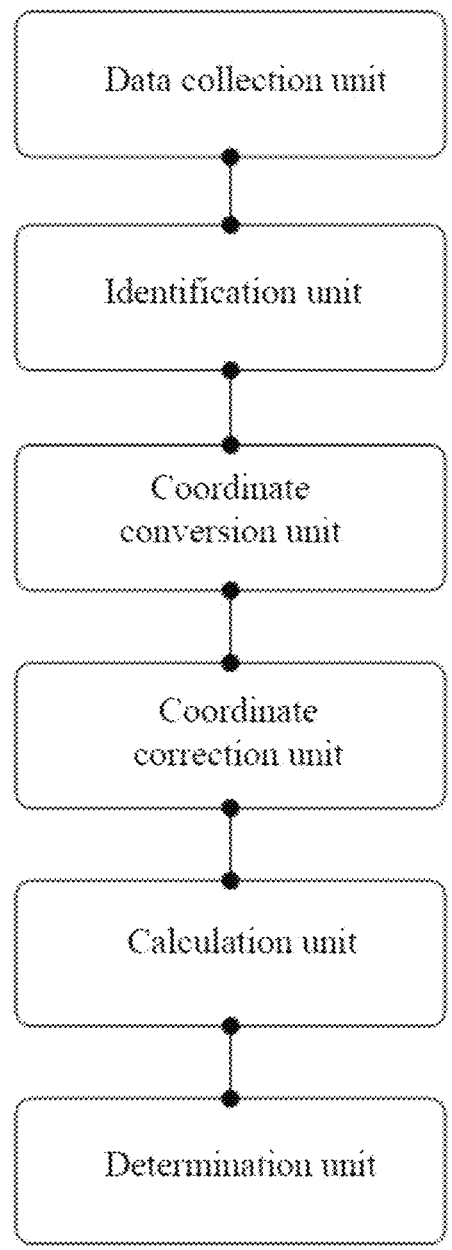
FIG. 7 is a schematic structural diagram of an apparatus for determining the validity of an EMG signal provided by an example of the present application.

Referring to FIG. 7, an example of the present application further provides an apparatus for determining the validity of an EMG signal, including:
- a data collection unit, configured to collect video data including squatting and foot-padding by dynamic muscle stimulation of a leg;
- an identification unit, configured to perform human body recognition on each frame of images of the video data, and acquire normalized coordinates of human body key points in each frame of images;
- a coordinate conversion unit, configured to convert the normalized coordinates of the human body key points in each frame of images into pixel coordinates to obtain the pixel coordinates of the human body key points in each frame of images;
- a coordinate correction unit, configured to correct the pixel coordinates of the human body key points in each frame of images according to shooting angles to obtain the corrected pixel coordinates of the key points in each frame of images;
- a calculation unit, configured to calculate a leg angle in each frame of images according to the corrected pixel coordinates of the key points in each frame of images to obtain angle data, the leg angles including a thigh bending angle and a foot-padding angle; and
- a determination unit, configured to determine whether the EMG signal is valid through the angle data.

As a further improvement, the apparatus further includes:
an optimization unit, configured to optimize the angle data;
the optimization unit is specifically used for:
dividing the angle data in each period into a rising signal and a falling signal, and constructing a state prediction equation of the rising signal and a state prediction equation of the falling signal in each period;
constructing a covariance matrix, an observation noise matrix and a measurement matrix;
calculating a filtering gain by the covariance matrix, the observation noise matrix and the measurement matrix;
optimizing the state prediction equation in a current period by the filtering gain; and
updating the covariance matrix and returning the step of calculating the filtering gain by the covariance matrix, the observation noise matrix and the measurement matrix until the angle data in all periods is optimized.

In an example of the present application, the video data of leg movements are collected at the same time as the EMG signals, and the angle data of the leg is acquired through the video data, and the validity of the collected EMG signal is determined through the angle data, to determine the collection quality of the EMG signal and improve the accuracy of the subsequent EMG signal processing. In the present application, it is further considered that the coordinates of key points obtained by human body recognition are normalized coordinates, and a coordinate system of each of frames is transformed. If the leg angle is calculated directly based on the normalized coordinates, there is a problem of complicated calculation process. In order to improve this problem, the normalized coordinates are converted into pixel coordinates, and the shooting error is corrected by the shooting angle. At this time, a pixel coordinate system of each of frames is fixed, which simplifies the calculation process of leg angles and improves the calculation efficiency.

An example of the present application also provides an electronic device, including a processor and a memory,
the memory being configured to store a program code and transmit the program code to the processor; and
the processor being configured to execute a method for determining the validity of an EMG signal in the foregoing method example according to the instructions in the program code.

An example of the present application also provides a computer-readable storage medium for storing a program code which, when executed by a processor, implements a method for determining the validity of an EMG signal in the foregoing method example.

It can be clearly understood by those skilled in the art that for the convenience and conciseness of description, the specific working processes of the above-described apparatus and units can refer to the corresponding processes in the above-mentioned method examples and will not be repeated here.

The terms "first", "second", "third", "fourth", and the like in the description of the present application and in the preceding figures, if any, are used for distinguishing between similar objects and not necessarily for describing a particular sequential or chronological order. It is to be understood that the data so used are interchangeable under appropriate circumstances, such that the examples of the present application described herein can, for example, be implemented in other orders than those illustrated or described herein.

Furthermore, the terms "include" and "have", as well as any variations thereof, are intended to cover a non-exclusive inclusion, such that a process, method, system, article, or device that includes a list of steps or elements is not necessarily limited to those steps or elements expressly listed, but may include other steps or elements not expressly listed or inherent to such processes, methods, articles, or apparatuses.

It is to be understood that in the present application, "at least one (item)" means one or more, and "plurality" means two or more. "And/or", used to describe an associated relationship of an associated object, means that there may be three relationships, for example, "A and/or B" may mean: there are only A, only B and both A and B, where A and B can be singular or plural. A character "/" generally indicates that the associated object is an "or" relationship. "At least one of the following one (item)" or similar expression thereof refers to any combination of these items, including any combination of single one (item) or plurality (items). For example, at least one (item) of a, b or c may represent: a, b, c, "a and b", "a and c", "b and c", or "a, b and c", where a, b and c may be single or multiple.

In the several examples provided in the present application, it is to be understood that the disclosed apparatus and method may be implemented in other ways. For example, the apparatus examples described above are merely illustrative, for example, the division of the units is only a logical function division, and there may be another division method in actual implementation, for example, multiple units or components may be combined or integrated into another system, or some features may be ignored or not implemented. In another aspect, the couplings or direct couplings or communication connections shown or discussed with respect to each other may be indirect couplings or communication connections through some interface, apparatus, or unit, and may be electrical, mechanical, or otherwise.

The units illustrated as separate elements may or may not be physically separated, and the elements shown as units may or may not be physical units, that is, the units and elements may be located in one place or may also be distributed on a plurality of network units. Some or all of the units may be selected to achieve the objectives of the example solutions according to actual needs.

In addition, each functional unit in each example of the present application can be integrated into one processing unit, or each unit can exist physically alone, or two or more units can be integrated into one unit. The above integrated units can be realized in the form of hardware or software functional units.

The integrated unit may be stored in a computer-readable storage medium if implemented as a software functional unit and sold or used as a stand-alone product. Based on such an understanding, the technical solution of the present application, either substantively or in any part contributing to the prior art, or all or part of the technical solution, can be embodied in the form of a software product stored in one storage medium, including a plurality of instructions for executing all or part of the steps of the method described in various examples of the present application through a computer device (which can be a personal computer, a server, a network device, etc.). The aforementioned storage medium includes: a universal serial bus (USB) flash disk, a mobile hard disk, a read-only memory (ROM), a random access memory (RAM), magnetic or optical disks and the like, which can store program codes.

As described above, the above examples are only used to illustrate the technical solutions of the present application, but not to limit this. Although the present application has been described in detail with reference to the foregoing examples, the technical solutions described in the foregoing examples can still be modified, or some technical features can be replaced by equivalents; while these modifications or substitutions do not make the essence of the corresponding technical solutions deviate from the spirit and scope of the technical solutions of various examples of the present application.

The invention claimed is:

1. A method for determining the validity of an electromyographic (EMG) signal, comprising:
   collecting video data comprising squatting and foot-padding by dynamic muscle stimulation of a leg, and collecting an EMG signal on a surface of the leg while squatting and foot-padding;
   performing human body recognition on each frame of images of the video data, and acquiring normalized coordinates of human body key points in each frame of images;
   converting the normalized coordinates of the human body key points in each frame of images into pixel coordinates to obtain the pixel coordinates of the human body key points in each frame of images;
   correcting the pixel coordinates of the human body key points in each frame of images according to shooting angles to obtain the corrected pixel coordinates of the key points in each frame of images;
   calculating a leg angle in each frame of images according to the corrected pixel coordinates of the key points in each frame of images to obtain angle data, the leg angles comprising a thigh bending angle and a foot-padding angle;
   calculating the thigh bending angle in each frame of images according to the corrected pixel coordinates of the key points in each frame of images, comprising:
   acquiring pixel coordinates of hip joint key points, pixel coordinates of ankle key points and pixel coordinates of knee key points in each frame of images from the corrected pixel coordinates of the key points in each frame of images;
   calculating three segments of distances among three key points of the hip joint, ankle and knee in each frame of images according to the pixel coordinates of the hip joint key points, the pixel coordinates of the ankle key points and the pixel coordinates of the knee key points in each frame of images; and
   calculating the thigh bending angle in each frame of images according to the three segments of distances among the three key points of the hip joint, ankle and knee in each frame of images; and
   calculating the foot-padding angle in each frame of images according to the corrected pixel coordinates of the key points in each frame of images, comprising:
   acquiring pixel coordinates of heel key points in each frame of images from the corrected pixel coordinates of the key points in each frame of images; and
   calculating the foot-padding angle in each frame of images according to the pixel coordinates of the heel key points in each frame of images; and
   determining whether the EMG signal is valid through the angle data, comprising:
   determining whether the EMG signal is valid according to angle change curve graphs of the thigh bending angle and the foot-padding angle, if the angle change curve graphs of the thigh bending angle and the foot-padding angle exhibit periodicity, the EMG signal being determined to be valid; and if the angle change curve graphs of the thigh bending angle and the foot-padding angle exhibit non-periodicity, the EMG signal being determined to be invalid.

2. The method for determining the validity of an EMG signal according to claim 1, wherein the converting the normalized coordinates of the human body key points in each frame of images into pixel coordinates to obtain the pixel coordinates of the human body key points in each frame of images comprises:
   converting, according to a length and a width of each frame of images, the normalized coordinates of the human body key points in each frame of images into the pixel coordinates to obtain the pixel coordinates of the human body key points in each frame of images.

3. The method for determining the validity of an EMG signal according to claim 1, wherein the correcting the pixel coordinates of the human body key points in each frame of images according to shooting angles to obtain the corrected pixel coordinates of the key points in each frame of images comprises:
   calculating a ratio of a vertical coordinate value of the pixel coordinate of the human body key point in each frame of images to a cosine value corresponding to the shooting angle to obtain the corrected pixel coordinates of the key points in each frame of images.

4. The method for determining the validity of an EMG signal according to claim 1, wherein the calculating a leg angle in each frame of images according to the corrected pixel coordinates of the key points in each frame of images to obtain angle data further comprises:
  optimizing the angle data, specifically comprising:
  dividing the angle data in each period into a rising signal and a falling signal, and constructing a state prediction equation of the rising signal and a state prediction equation of the falling signal in each period;
  constructing a covariance matrix, an observation noise matrix and a measurement matrix;
  calculating a filtering gain by the covariance matrix, the observation noise matrix and the measurement matrix;
  optimizing the state prediction equation in a current period by the filtering gain; and
  updating the covariance matrix and returning the step of calculating the filtering gain by the covariance matrix, the observation noise matrix and the measurement matrix until the angle data in all periods is optimized.

5. The method for determining the validity of an EMG signal according to claim 2, wherein the calculating a leg angle in each frame of images according to the corrected pixel coordinates of the key points in each frame of images to obtain angle data further comprises:
  optimizing the angle data, specifically comprising:
  dividing the angle data in each period into a rising signal and a falling signal, and constructing a state prediction equation of the rising signal and a state prediction equation of the falling signal in each period;
  constructing a covariance matrix, an observation noise matrix and a measurement matrix;
  calculating a filtering gain by the covariance matrix, the observation noise matrix and the measurement matrix;
  optimizing the state prediction equation in a current period by the filtering gain; and
  updating the covariance matrix and returning the step of calculating the filtering gain by the covariance matrix, the observation noise matrix and the measurement matrix until the angle data in all periods is optimized.

6. The method for determining the validity of an EMG signal according to claim 3, wherein the calculating a leg angle in each frame of images according to the corrected pixel coordinates of the key points in each frame of images to obtain angle data further comprises:
  optimizing the angle data, specifically comprising:
  dividing the angle data in each period into a rising signal and a falling signal, and constructing a state prediction equation of the rising signal and a state prediction equation of the falling signal in each period;
  constructing a covariance matrix, an observation noise matrix and a measurement matrix;
  calculating a filtering gain by the covariance matrix, the observation noise matrix and the measurement matrix;
  optimizing the state prediction equation in a current period by the filtering gain; and
  updating the covariance matrix and returning the step of calculating the filtering gain by the covariance matrix, the observation noise matrix and the measurement matrix until the angle data in all periods is optimized.

7. The method for determining the validity of an EMG signal according to claim 4, wherein the updating the covariance matrix comprises:
  determining whether a current moment is at a boundary point of the current period, if not, a current covariance matrix being updated according to a current filtering gain and the measurement matrix; and if so, a current covariance matrix being updated as an initial value of the covariance matrix.

8. An apparatus for determining the validity of an EMG signal, comprising:
  a data collection unit, configured to collect video data comprising squatting and foot-padding by dynamic muscle stimulation of a leg, and collect an EMG signal on a surface of the leg while squatting and foot-padding;
  an identification unit, configured to perform human body recognition on each frame of images of the video data, and acquire normalized coordinates of human body key points in each frame of images;
  a coordinate conversion unit, configured to convert the normalized coordinates of the human body key points in each frame of images into pixel coordinates to obtain the pixel coordinates of the human body key points in each frame of images;
  a coordinate correction unit, configured to correct the pixel coordinates of the human body key points in each frame of images according to shooting angles to obtain the corrected pixel coordinates of the key points in each frame of images;
  a calculation unit, configured to calculate a leg angle in each frame of images according to the corrected pixel coordinates of the key points in each frame of images to obtain angle data, the leg angles comprising a thigh bending angle and a foot-padding angle;
  wherein to calculate the thigh bending angle in each frame of images according to the corrected pixel coordinates of the key points in each frame of images, the calculation unit is configured to comprising:
  acquire pixel coordinates of hip joint key points, pixel coordinates of ankle key points and pixel coordinates of knee key points in each frame of images from the corrected pixel coordinates of the key points in each frame of images;
  calculate three segments of distances among three key points of the hip joint, ankle and knee in each frame of images according to the pixel coordinates of the hip joint key points, the pixel coordinates of the ankle key points and the pixel coordinates of the knee key points in each frame of images; and
  calculate the thigh bending angle in each frame of images according to the three segments of distances among the three key points of the hip joint, ankle and knee in each frame of images; and
  wherein to calculate the foot-padding angle in each frame of images according to the corrected pixel coordinates of the key points in each frame of images, the calculation unit is configured to comprising:
  acquire pixel coordinates of heel key points in each frame of images from the corrected pixel coordinates of the key points in each frame of images; and
  calculate a foot-padding angle in each frame of images according to the pixel coordinates of the heel key points in each frame of images; and
  a determination unit, configured to determine whether the EMG signal is valid through the angle data, comprising:
  determining whether the EMG signal is valid according to angle change curve graphs of the thigh bending angle and the foot-padding angle, if the angle change curve graphs of the thigh bending angle and the foot-padding angle exhibit periodicity, the EMG signal being determined to be valid; and if the angle change curve graphs of the thigh bending angle and the foot-padding angle exhibit non-periodicity, the EMG signal being determined to be invalid.

9. An electronic device, comprising a processor and a memory,
the memory being configured to store a program code and transmit the program code to the processor; and
the processor being configured to execute the method for determining the validity of an EMG signal according to claim 1 according to instructions in the program code.

10. An electronic device, comprising a processor and a memory,
the memory being configured to store a program code and transmit the program code to the processor; and
the processor being configured to execute the method for determining the validity of an EMG signal according to claim 2 according to instructions in the program code.

11. An electronic device, comprising a processor and a memory,
the memory being configured to store a program code and transmit the program code to the processor; and
the processor being configured to execute the method for determining the validity of an EMG signal according to claim 3 according to instructions in the program code.

12. An electronic device, comprising a processor and a memory,
the memory being configured to store a program code and transmit the program code to the processor; and
the processor being configured to execute the method for determining the validity of an EMG signal according to claim 4 according to instructions in the program code.

13. An electronic device, comprising a processor and a memory,
the memory being configured to store a program code and transmit the program code to the processor; and
the processor being configured to execute the method for determining the validity of an EMG signal according to claim 5 according to instructions in the program code.

14. A non-transitory computer-readable storage medium for storing a program code which, when executed by a processor, implements the method for determining the validity of an EMG signal according to claim 1.

15. A non-transitory computer-readable storage medium for storing a program code which, when executed by a processor, implements the method for determining the validity of an EMG signal according to claim 2.

16. A non-transitory computer-readable storage medium for storing a program code which, when executed by a processor, implements the method for determining the validity of an EMG signal according to claim 3.

17. A non-transitory computer-readable storage medium for storing a program code which, when executed by a processor, implements the method for determining the validity of an EMG signal according to claim 4.

18. A non-transitory computer-readable storage medium for storing a program code which, when executed by a processor, implements the method for determining the validity of an EMG signal according to claim 5.

* * * * *